US00PP32727P2

(12) United States Plant Patent
von Tubeuf

(10) Patent No.: US PP32,727 P2
(45) Date of Patent: Jan. 5, 2021

(54) POINSETTIA PLANT NAMED 'NPCW19280'

(50) Latin Name: *Euphorbia pulcherrima*
Varietal Denomination: NPCW19280

(71) Applicant: Klemm+Sohn GmbH & Co. KG, Stuttgart (DE)

(72) Inventor: Guido von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 16/873,128

(22) Filed: Feb. 6, 2020

(51) Int. Cl.
*A01H 5/02* (2018.01)
*A01H 6/38* (2018.01)

(52) U.S. Cl.
USPC ..... Plt./307

(58) Field of Classification Search
USPC ..... Plt./307
See application file for complete search history.

*Primary Examiner* — Annette H Para
(74) *Attorney, Agent, or Firm* — Weatherly IP Solutions, LLC; James Weatherly

(57) ABSTRACT

A new poinsettia plant particularly distinguished by having a medium vigor, orbicular leaf shape and an orbicular bract shape, is disclosed.

1 Drawing Sheet

Genus and species: *Euphorbia pulcherrima.*
Variety denomination: 'NPCW19280'.

BACKGROUND OF THE NEW PLANT

The present invention comprises a new and distinct variety of poinsettia, botanically known as *Euphorbia pulcherrima* and hereinafter referred to by the variety name 'NPCW19280'. 'NPCW19280' derived as a selection of a single plant showing rounded bracts and foliage among a population derived from irradiated cuttings of the commercial variety 'Vesuvio' (Non Patented).

In April 2011 cuttings of the variety 'Vesuvio' were irradiated in JKI Quedlinburg, Germany and plants were grown for evaluation. A plant line was selected in November 2013 in Stuttgart, Germany and named 'NPCW19280'. In February 2014, 'NPCW19280' was first vegetatively propagated by vegetative cuttings. 'NPCW19280' was found to reproduce true to type in successive generations of asexual propagation via apical cuttings in Stuttgart, Germany.

SUMMARY

The following are the most outstanding and distinguishing characteristics of this new variety when grown under normal horticultural practices in Stuttgart, Germany.

1. Obtuse bracts;
2. Obtuse leaves; and
3. Very high vigor.

DESCRIPTION OF THE PHOTOGRAPH

This new poinsettia plant is illustrated by the accompanying photograph which shows an overall view of the plant. The photograph is of a plant approximately twelve-weeks-old grown indoors Stuttgart, Germany in December 2016. The colors shown are as true as can be reasonably obtained by conventional photographic procedures.

DESCRIPTION OF THE NEW VARIETY

The following detailed descriptions set forth the distinctive characteristics of 'NPCW19280'. The data which define these characteristics were collected from asexual reproductions carried out in Stuttgart, Germany. Data was collected on four-month-old plants grown indoors in Stuttgart, Germany under greenhouse conditions in November of 2019. Color references are to The R.H.S. Colour Chart of The Royal Horticultural Society of London (R.H.S.), 5$^{th}$ edition (2007).

Classification:
- *Family.*—Euphorbiaceae.
- *Species.*—*Euphorbia pulcherrima.*
- *Common name.*—Poinsettia.
- *Variety.*—'NPCW19280'.

Parentage:
- *Male.*—None.
- *Female.*—Selection from irradiated cuttings of the commercial variety 'Vesuvio' (U.S. Plant Pat. No. 23,925).

Plant:
- *Form.*—Triangular.
- *Growth habit.*—Upright.
- *Height.*—20.0 cm to 22.0 cm.
- *Width.*—30.0 cm to 33.0 cm.
- *Average number of inflorescences per plant.*—5.
- *Keeping quality.*—Very good.
- *Time to produce a cutting.*—5 to 6 weeks.
- *Blooming habit.*—Intermittent.
- *Flowering response time.*—Approximately 55 days.
- *Disease and pest resistance.*—None observed.

Propagation:
- *Type cuttings.*—Apical cuttings.
- *Time to produce a rooted cutting.*—4 weeks.
- *Rooting habit and root color.*—Freely branching and white.

Lateral branches:
- *Color.*—RHS 143A.
- *Length.*—17.0 cm to 20.0 cm.
- *Internode length.*—0.5 cm to 3.0 cm.
- *Diameter.*—0.3 cm to 0.5 cm.
- *Branching habit.*—Freely branching.

*Number of lateral branches per plant.*—4 to 5.
*Texture.*—Smooth.

Leaves:
*Quantity.*—5 to 6 per lateral branch.
*Arrangement.*—Alternate.
*Number of lobes on the leaf blade.*—None.
*Shape.*—Orbicular.
*Apex.*—Obtuse.
*Base.*—Rounded.
*Margin.*—Entire.
*Length.*—6.0 cm to 8.0 cm.
*Width.*—6.0 cm to 8.0 cm.
*Texture (both surfaces).*—Smooth.
*Vein color.*—Upper surface: Transparent. Lower surface: RHS 139D, main vein slightly reddish on the lower part.
*Variegation.*—Absent.
*Venation pattern.*—Reticulate.
*Color.*—Mature foliage: Upper surface: RHS 139A. Lower surface: RHS 139D. Immature foliage: Upper surface: RHS 141A. Lower surface: RHS 139B.
*Leaf petiole.*—Length: 3.0 cm to 4.0 cm. Diameter: 0.2 cm to 0.3 cm. Color: Upper (part) surface: RHS 59A. Lower (part) surface: RHS 181B. Texture: Smooth. Strength: Medium.

Inflorescence:
*Lastingness of inflorescence on the plant.*—4 to 5 weeks.
*Natural flowering season.*—End of November.
*Diameter.*—14.0 cm to 16.0 cm.
*Height.*—2.0 cm to 3.0 cm.
*Fragrance.*—Absent.

Bracts:
*Number of bracts per inflorescence.*—7 to 8.
*Shape.*—Between orbicular and ovate.
*Apex.*—Obtuse.
*Base.*—Rounded.
*Margin.*—Entire.
*Size.*—Length: 4.0 cm to 8.0 cm. Width: 3.0 cm to 6.0 cm.
*Texture (both upper and lower surfaces).*—Smooth.
*Venation pattern.*—Reticulate.
*Vein color.*—Upper surface: RHS 59A. Lower surface: RHS 181B.
*Bract color.*—Upper surface: Between RHS 46A and RHS 46B. Lower surface: Close to RHS 53B.
*Bract petiole.*—Length: 0.5 cm to 1.0 cm. Diameter: 0.2 cm. Color: Upper (part) surface: RHS 59A. Lower (part) surface: RHS 181B. Texture: Smooth. Strength: Medium.

Cyme:
*Diameter.*—1.0 cm to 1.5 cm.
*Cyathia number.*—5.0 cm to 6.0 cm per inflorescence.
*Deformation of glands of the cyathium.*—Absent.
*Timing of opening of cyathia.*—Opens end of November; first pollen appears in parallel to opening of the nectar cups, stigmas arrive 2 weeks later.
*Cyathium.*—Shape: Ovate. Diameter: 0.2 cm to 0.5 cm. Length: 0.3 cm to 0.7 cm. Color: RHS 143C.
*Peduncle.*—Color: RHS 142B. Length: 0.2 cm. Diameter: 0.1 cm. Texture: Smooth. Strength: Medium.
*Nectar cups.*—Number: 1 per cyathium. Diameter: 0.1 cm. Length: 0.3 cm to 0.4 cm. Color: RHS 12A.

Reproductive organs:
*Stamen quantity.*—5 to 8 per cyathium.
*Stamen shape.*—Ovate.
*Filament length.*—0.25 cm.
*Filament color.*—RHS 46A.
*Pollen quantity.*—Sparse.
*Pollen color.*—RHS 12A.
*Gynoecium.*—Present. Pistil quantity per cyathium: 1. Pistil length: 0.2 cm. Stigma form: Divided in 2 parts. Stigma color: RHS 183A. Style length 0.2 cm. Style color: RHS 183A. Ovary length: 0.2 cm. Ovary color: RHS 143C.

Fruit and seed set: Not observed.

COMPARISON WITH PARENTAL LINE AND KNOWN VARIETY

'NPCW19280' is distinguished from its mutation parent as described in Table 1:

TABLE 1

Comparison with Parental Lines

| Characteristic | Variety 'NPCW19280' | Mutation parent 'Vesuvio' |
|---|---|---|
| Vigor | Medium | Very high |
| Leaf shape | Orbicular | Obtuse |
| Bract shape | Orbicular | Obtuse |

COMPARISON WITH SIMILAR VARIETY

Applicant respectfully submits that there are no commercially similar varieties available for comparison.

I claim:

1. A new and distinct variety of poinsettia plant named 'NPCW19280' as shown and described herein.

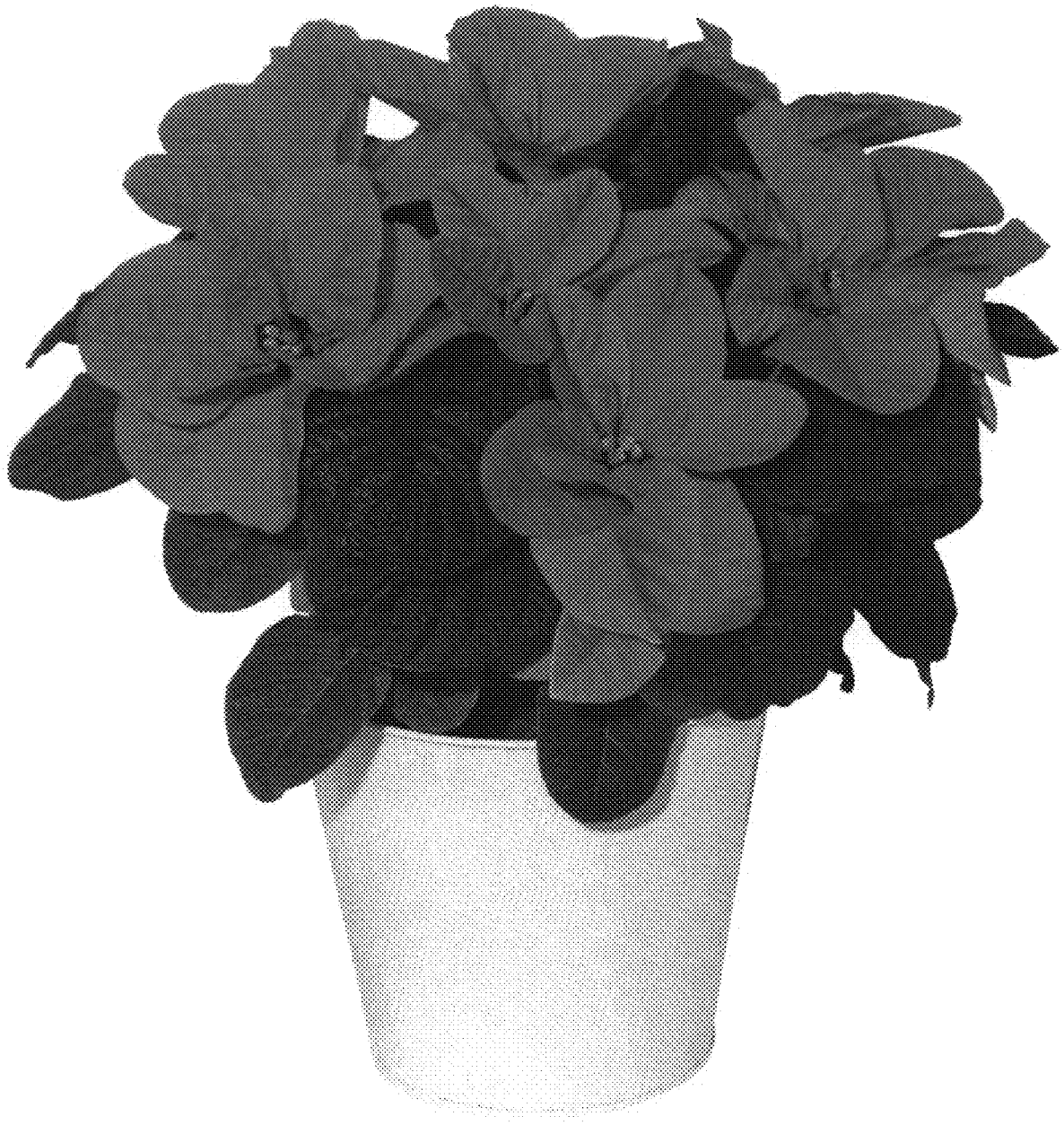

* * * * *